United States Patent
Popovic et al.

(10) Patent No.: US 9,280,823 B2
(45) Date of Patent: Mar. 8, 2016

(54) INVISIBLE BIFURCATION DETECTION WITHIN VESSEL TREE IMAGES

(71) Applicant: KONINKLIJKE PHILIPS N.V., Eindhoven (NL)

(72) Inventors: Aleksandra Popovic, New York, NY (US); Haytham Elhawary, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 29 days.

(21) Appl. No.: 14/376,318

(22) PCT Filed: Feb. 4, 2013

(86) PCT No.: PCT/IB2013/050938
§ 371 (c)(1),
(2) Date: Aug. 1, 2014

(87) PCT Pub. No.: WO2013/118047
PCT Pub. Date: Aug. 15, 2013

(65) Prior Publication Data
US 2015/0010225 A1 Jan. 8, 2015

Related U.S. Application Data

(60) Provisional application No. 61/595,315, filed on Feb. 6, 2012.

(51) Int. Cl.
*G06K 9/00* (2006.01)
*G06T 7/00* (2006.01)
*A61B 1/00* (2006.01)

(52) U.S. Cl.
CPC ............... *G06T 7/003* (2013.01); *A61B 1/0005* (2013.01); *A61B 1/00009* (2013.01);
(Continued)

(58) Field of Classification Search
USPC .................................. 382/128, 131, 284, 294
See application file for complete search history.

(56) References Cited

U.S. PATENT DOCUMENTS 7,689,019 B2    3/2010   Boese et al.
7,983,459 B2 *  7/2011   Begelman ............ G06K 9/3241
                                                345/418
(Continued)

FOREIGN PATENT DOCUMENTS

WO    2008111070    9/2008
WO    2010046802    4/2010
(Continued)

*Primary Examiner* — John Strege

(57) ABSTRACT

An image registration system an endoscope (12) and an endoscope controller (22). In operation, the endoscope (12) generates an intra-operative endoscopic image (14) of a vessel tree within an anatomical region including a plurality of branches of the vessel tree visible within the intra-operative endoscopic image (14) as an indication of a furcation of the vessel tree invisible within the intra-operative endoscopic image (14). The endoscope controller (22) image registers the intra-operative operative endoscopic image (14) of the vessel tree to a pre-operative three-dimensional image (44) of the vessel tree. The image registration includes an image matching of a graphical representation of the furcation of the vessel tree as indicated by the branches of the vessel tree visible within the intra-operative endoscopic image (14) of the vessel tree to a graphical representation of the furcation of the vessel tree visible within the pre-operative three-dimensional image (44) of the vessel tree.

15 Claims, 9 Drawing Sheets

(52) U.S. Cl.
CPC .. *G06T 2200/04* (2013.01); *G06T 2207/10068* (2013.01); *G06T 2207/10072* (2013.01); *G06T 2207/20072* (2013.01); *G06T 2207/30101* (2013.01)

(56) References Cited

U.S. PATENT DOCUMENTS

| | | | | |
|---|---|---|---|---|
| 8,821,376 | B2* | 9/2014 | Tolkowsky | A61B 1/0052 600/101 |
| 2005/0027193 | A1 | 2/2005 | Mitschke et al. | |
| 2007/0217665 | A1* | 9/2007 | Kiraly | G06K 9/6892 382/128 |
| 2008/0247622 | A1* | 10/2008 | Aylward | A61B 19/52 382/131 |
| 2008/0249755 | A1* | 10/2008 | Tek | A61B 5/02014 703/11 |
| 2009/0060298 | A1* | 3/2009 | Weijers | G06T 7/0012 382/128 |
| 2009/0163800 | A1 | 6/2009 | Xu et al. | |
| 2010/0041949 | A1* | 2/2010 | Tolkowsky | A61B 1/0052 600/109 |
| 2010/0061611 | A1* | 3/2010 | Xu | G06T 7/003 382/131 |
| 2011/0033102 | A1* | 2/2011 | Zhu | G06T 7/0016 382/134 |
| 2013/0165948 | A1* | 6/2013 | Popovic | A61B 1/0005 606/130 |
| 2014/0355858 | A1* | 12/2014 | O'Dell | G06T 7/0081 382/131 |

FOREIGN PATENT DOCUMENTS

| | | |
|---|---|---|
| WO | 2010133982 | 11/2010 |
| WO | 2012035492 | 3/2012 |

* cited by examiner

INVISIBLE BIFURCATION DETECTION WITHIN VESSEL TREE IMAGES

CROSS-REFERENCE TO PRIOR APPLICATIONS

This application is the U.S. National Phase application under 35 U.S.C. §371 of International Application Serial No. PCT/IB2013/050938, filed on Feb. 4, 2013, which claims the benefit of U.S. Application Ser. No. 61/595,315, filed on Feb. 6, 2012. These applications are hereby incorporated by reference herein.

This application claims benefit to of the commonly-owned Patent Application entitled "Robotic Control of An Endoscope From Vessel Tree Images".

The present invention generally relates to an intra-operative registration between a pre-operative three-dimensional ("3D") vessel tree image to an intra-operative endoscopic vessel tree image(s). The present invention specifically relates to the intra-operative registration incorporating methods for detecting bifurcations of the vessel tree that are not visible (i.e., invisible) in the endoscopic image(s) due to fatty tissue covering the surface of an organ (e.g., a heart).

Coronary artery bypass grafting ("CABG") is a surgical procedure for revascularization of obstructed coronary arteries. Approximately 500,000 operations are performed annually in the United States. In conventional CABG, the patient's sternum is opened and the patient's heart is fully exposed to a surgeon. Despite the exposure of the heart, some arteries may be invisible due to fatty tissue layer above them. For such arteries, the surgeon may palpate the heart surface and feel both blood pulsating from the arteries and a stenosis of the arteries. However, this data is sparse and might not be sufficient to transfer a surgical plan to the surgical site.

In minimally invasive CABG, the aforementioned problem of conventional CABG is amplified because a surgeon cannot palpate the heart surface. Additionally, the length of surgical instruments used in minimally invasive CABG prevents any tactile feedback from the proximal end of the tool.

One known technique for addressing the problems with conventional CABG is to register an intra-operative site with a pre-operative 3D coronary artery tree. Specifically, an optically tracked pointer is used to digitalize position of the arteries in an open heart setting and the position data is registered to the pre-operative tree using an Iterative Closest Point ("ICP") algorithm known in art. However, this technique, as with any related approach matching digitized arteries and pre-operative data, is impractical for minimally invasive CABG because of spatial constraints imposed by a small port access. Also, this technique requires most of the arteries to be either visible or palpated by the surgeon, which is impossible in minimally invasive CABG.

One known technique for addressing the problems with minimally invasive CABG is to implement a registration method in which the heart surface is reconstructed using an optically tracked endoscope and matched to pre-operative computer tomography ("CT") data of the same surface. However, this technique, as with any related approach proposing surface based matching, may fail if the endoscope view used to derive the surface is too small. Furthermore, as the heart surface is relatively smooth without specific surface features, the algorithm of this technique more often than not operates in a suboptimal local maximum of the algorithm.

Another known technique for addressing the problems with minimally invasive CABG is to label a coronary tree extracted from a new patient using a database of previously labeled cases and graph based matching. However, this technique works only if a complete tree is available and it's goal is to label the tree rather than to match the geometry.

A further problem of minimally invasive CABG is an orientation and a guidance of the endoscope once the global positioning with respect to pre-operative 3D images is reached. The goal of registration is to facilitate localization of the anastomosis site and the stenosis. In a standard setup, the endoscope is being held by an assistant, while the surgeon holds two instruments. The surgeon issues commands to the assistant and the assistant moves the endoscope accordingly. This kind of setup hinders hand-eye coordination of the surgeon, because the assistant needs to intuitively translate surgeon's commands, typically issued in the surgeon's frame of reference, to the assistant's frame of reference and the endoscope's frame of reference. Plurality of coordinate systems may cause various handling errors, prolong the surgery or cause misidentification of the coronary arteries.

A surgical endoscope assistant designed to allow a surgeon to directly control an endoscope via a sensed movement of the surgeon head may solve some of these problems by removing the assistant from the control loop, but the problem of transformation between the surgeon's frame of reference and the endoscope's frame of reference remains.

The present invention provides image registration methods for matching graphical representations each furcation of a vessel tree (e.g., each point of arteries, capillaries, veins and other multi-branched anatomical structures) as shown in a pre-operative three-dimensional ("3D") image (e.g., a CT image, a cone beam CT image, a 3D X-Ray images or a MRI image) and in an intra-operative endoscopic image. The image registration methods addresses bifurcations of the vessel tree that are not visible (i.e., invisible) in the endoscopic image(s) due to fatty tissue covering the surface of an organ (e.g., a heart).

For purposes of the present invention, the term "furcation" is broadly define herein as any point along a vessel tree that divides into two or more branches.

One form of the present invention is a registration system employing an endoscope and an endoscope controller. In operation, the endoscope generates an intra-operative endoscopic image of a vessel tree (e.g., an arterial tree, a venous tree or any other tubular structure of the human body) within an anatomical region, and the endoscope controller image registers the intra-operative operative endoscopic image of the vessel tree to a pre-operative three-dimensional image of the vessel tree. The intra-operative endoscopic image of the vessel tree includes a plurality of branches of the vessel tree visible within the intra-operative endoscopic image indicative of a furcation of the vessel tree invisible within the intra-operative endoscopic image. The image registration includes an image matching of a graphical representation of the furcation of the vessel tree as indicated by the branches of the vessel tree visible within the intra-operative endoscopic image of the vessel tree to a graphical representation of the furcation of the vessel tree within the pre-operative three-dimensional image of the vessel tree.

A second form of the present invention is an image registration method involving a generation of a pre-operative three-dimensional image of a vessel tree within an anatomical region, a generation of an intra-operative endoscopic image of the vessel tree within the anatomical region, and image registration of the intra-operative endoscopic image of the vessel tree to the pre-operative three-dimensional image of the vessel tree. The intra-operative endoscopic image of the vessel tree includes a plurality of branches of the vessel tree visible within the intra-operative endoscopic image indicative of a furcation of the vessel tree invisible within the intra-operative endoscopic image. The image registration includes an image matching of a graphical representation of the furcation of the vessel tree as indicated by the branches of the vessel tree visible within the intra-operative endoscopic image of the vessel tree to a graphical representation of the furcation of the vessel tree within the pre-operative three-dimensional image of the vessel tree.

The term "pre-operative" as used herein is broadly defined to describe any activity executed before, during or after an endoscopic imaging of an anatomical region for purposes of acquiring a three-dimensional image of the anatomical region, and the term "intra-operative" as used herein is broadly defined to describe any activity during or related to an endoscopic imaging of the anatomical region. Examples of an endoscopic imaging of an anatomical region include, but are not limited to, a CABG, a bronchoscopy, a colonscopy, a laparascopy, and a brain endoscopy.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
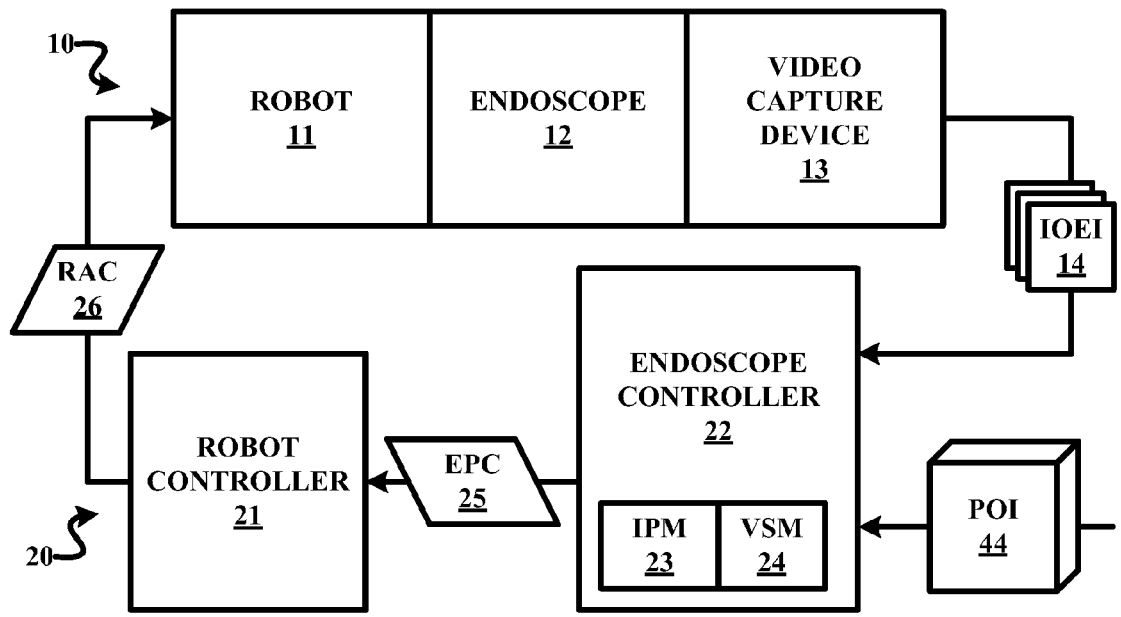
FIG. 1 illustrates an exemplary embodiment of a robotic guiding system in accordance with the present invention.

As shown in FIG. 1, a robotic guiding system employs a robot unit 10 and a control unit 20 for any endoscopic procedure involving an endoscopic imaging of a vessel tree having one or more furcations (i.e., branches). Examples of such endoscopic procedures include, but are not limited to, minimally invasive cardiac surgery (e.g., coronary artery bypass grafting or mitral valve replacement).

Robot unit 10 includes a robot 11, an endoscope 12 rigidly attached to robot 11 and a video capture device 13 attached to the endoscope 12.

Robot 11 is broadly defined herein as any robotic device structurally configured with motorized control of one or more joints for maneuvering an end-effector as desired for the particular endoscopic procedure. In practice, robot 11 may have four (4) degrees-of-freedom, such as, for example, a serial robot having joints serially connected with rigid segments, a parallel robot having joints and rigid segments mounted in parallel order (e.g., a Stewart platform known in the art) or any hybrid combination of serial and parallel kinematics.

Endoscope 12 is broadly defined herein as any device structurally configured with ability to image from inside a body. Examples of endoscope 12 for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thoracope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

In practice, endoscope 12 is mounted to the end-effector of robot 11. A pose of the end-effector of robot 11 is a position and an orientation of the end-effector within a coordinate system of robot actuators. With endoscope 12 mounted to the end-effector of robot 11, any given pose of the field-of-view of endoscope 12 within an anatomical region corresponds to a distinct pose of the end-effector of robot 11 within the robotic coordinate system. Consequently, each individual endoscopic image of a vessel tree generated by endoscope 12 may be linked to a corresponding pose of endoscope 12 within the anatomical region.

Video capture device 13 is broadly defined herein as any device structurally configured with a capability to convert an intra-operative endoscopic video signal from endoscope 12 into a computer readable temporal sequence of intra-operative endoscopic images ("IOEI") 14. In practice, video capture device 13 may employ a frame grabber of any type for capturing individual digital still frames from the intra-operative endoscopic video signal.

Still referring to FIG. 1, control unit 20 includes a robot controller 21 and an endoscope controller 22.

Robot controller 21 is broadly defined herein as any controller structurally configured to provide one or more robot actuator commands ("RAC") 26 to robot 11 for controlling a pose of the end-effector of robot 11 as desired for the endoscopic procedure. More particularly, robot controller 21 converts endoscope position commands ("EPC") 25 from endoscope controller 22 into robot actuator commands 26. For example, endoscope position commands 25 may indicate an endoscopic path leading to desired 3D position of a field-of-view of endoscope 12 within an anatomical region whereby robot controller 21 converts command 25 into commands 26 including an actuation current for each motor of robot 11 as needed to move endoscope 12 to the desired 3D position.

Figure 2:
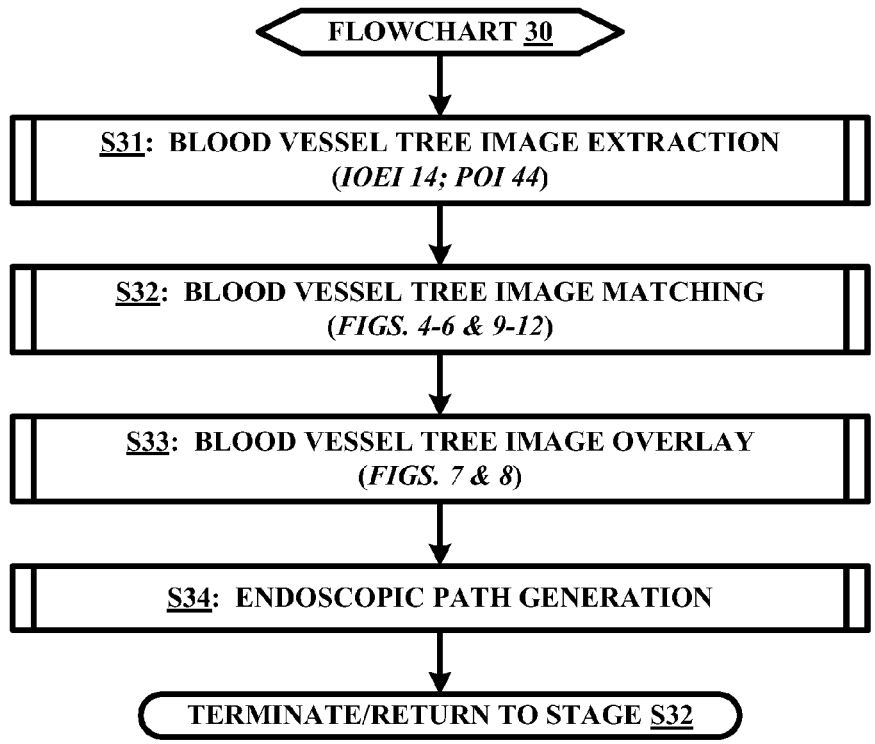
FIG. 2 illustrates a flowchart representative of an exemplary embodiment of a robotic guidance method in accordance with the present invention.

Endoscope controller 22 is broadly defined herein as any controller structurally configured for implementing a robotic guidance method in accordance with the present invention and exemplary shown in FIG. 2. To this end, endoscope controller 22 may incorporate an image processing module ("IPM") 23, which is broadly defined herein as any module structurally configured for executing an anatomical object image registration of the present invention. In particular, a vessel tree image registration as exemplarily implemented by stages S32 and S33 of flowchart 30 shown in FIG. 2. Endoscope controller 22 may further incorporate a visual servo module ("VSM") 24, which is broadly defined herein as any module structurally configured for generating endoscope position commands 25 indicating an endoscopic path leading to desired 3D position of a field-of-view of endoscope 12 within an anatomical region. In particular, endoscope position commands 25 are derived from the vessel tree image registration as exemplarily implemented by a stage S34 of flowchart 30 shown in FIG. 2.

A description of flowchart 30 will now be provided herein to facilitate a further understanding of endoscope controller 22.

Figure 3:
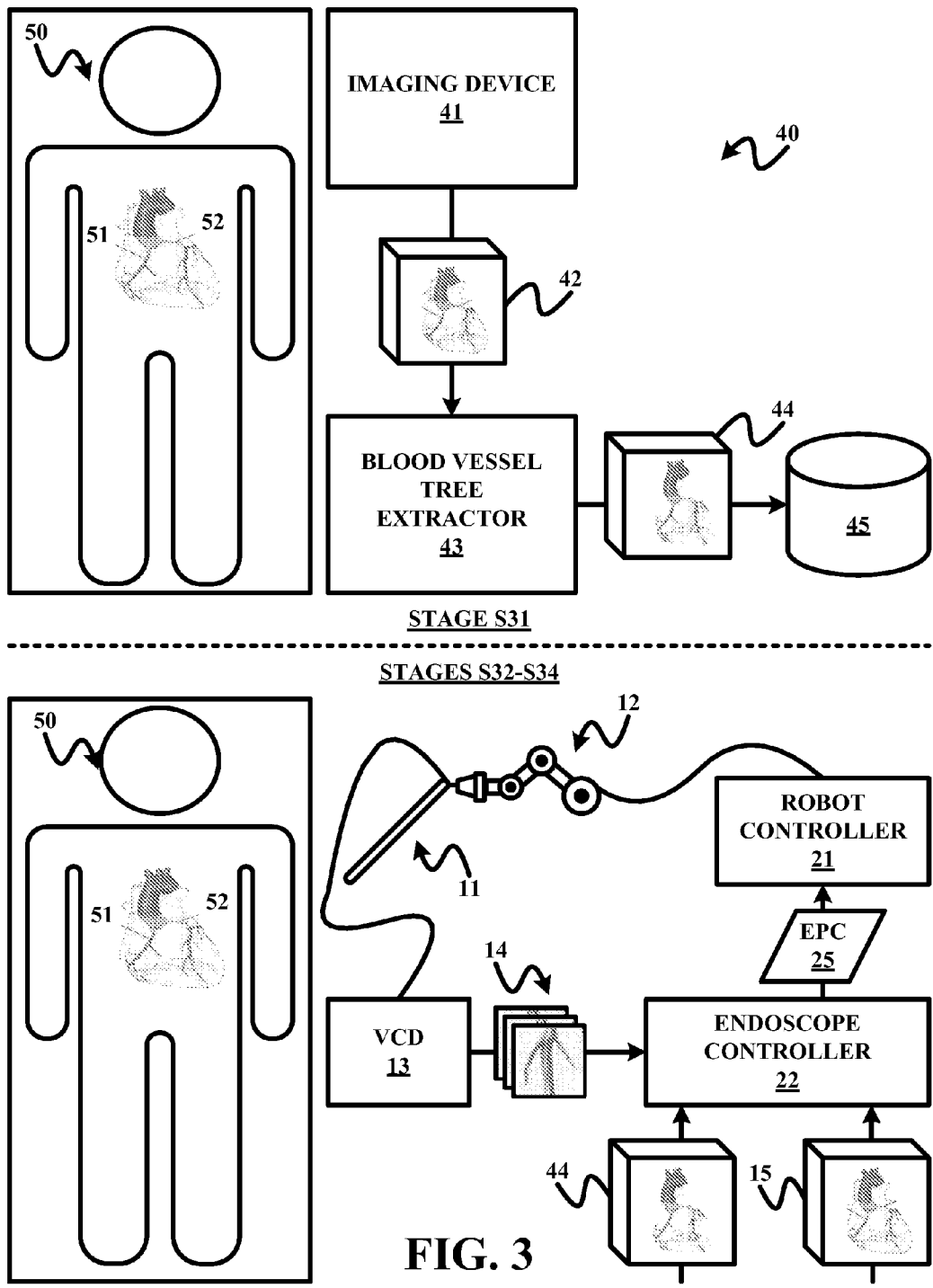
FIG. 3 illustrates an exemplary surgical implementation of the flowchart shown in FIG. 2

Referring to FIG. 2, a stage S31 of flowchart 30 encompasses an extraction of a geometrical representation of a vessel tree (e.g., furcation of arteries, capillaries or veins) from a pre-operative 3D image of any anatomical region of a body. For example, as shown in FIG. 3, a 3D imaging device (e.g., a CT device, an X-ray device, or a MRI device) is operated to generate a pre-operative 3D image 42 of a chest region of a patient 50 illustrating left and right coronary arteries 51 and 52 of patient 50. Thereafter, a vessel tree extractor 43 is operated to extract a geometrical representation 44 of a coronary arterial tree from image 42, which may be stored in a database 45. In practice, a Brilliance iCT scanner sold by Philips may be used to generate image 42 and to extract a 3D dataset of the coronary arterial tree from image 42.

Referring back to FIG. 2, a stage S32 of flowchart 30 encompasses image processing module 23 matching the graphical representation of one or more intra-operative endoscopic images 14 (FIG. 1) of the vessel tree to a graphical representation of pre-operative 3D image 44 (FIG. 1) of the vessel tree. For example, as shown in FIG. 3, endoscope 12 generates an intra-operative endoscopy video of a chest region of patient 50 that is captured by video capture device 13 and converted into intra-operative endoscopic images 14 whereby image processing module 23 of endoscope controller 22 matches a graphical representation of the intra-operative endoscopic image(s) 14 of the coronary arterial tree to a graphical representation of pre-operative 3D image 44 of the coronary arterial tree. In one exemplary embodiment, image processing module 23 executes a vessel tree image matching method of the present invention as exemplarily represented by a flowchart 60 shown in FIG. 4, which will be described herein in the context of the vessel tree being a coronary arterial tree.

Figure 4:
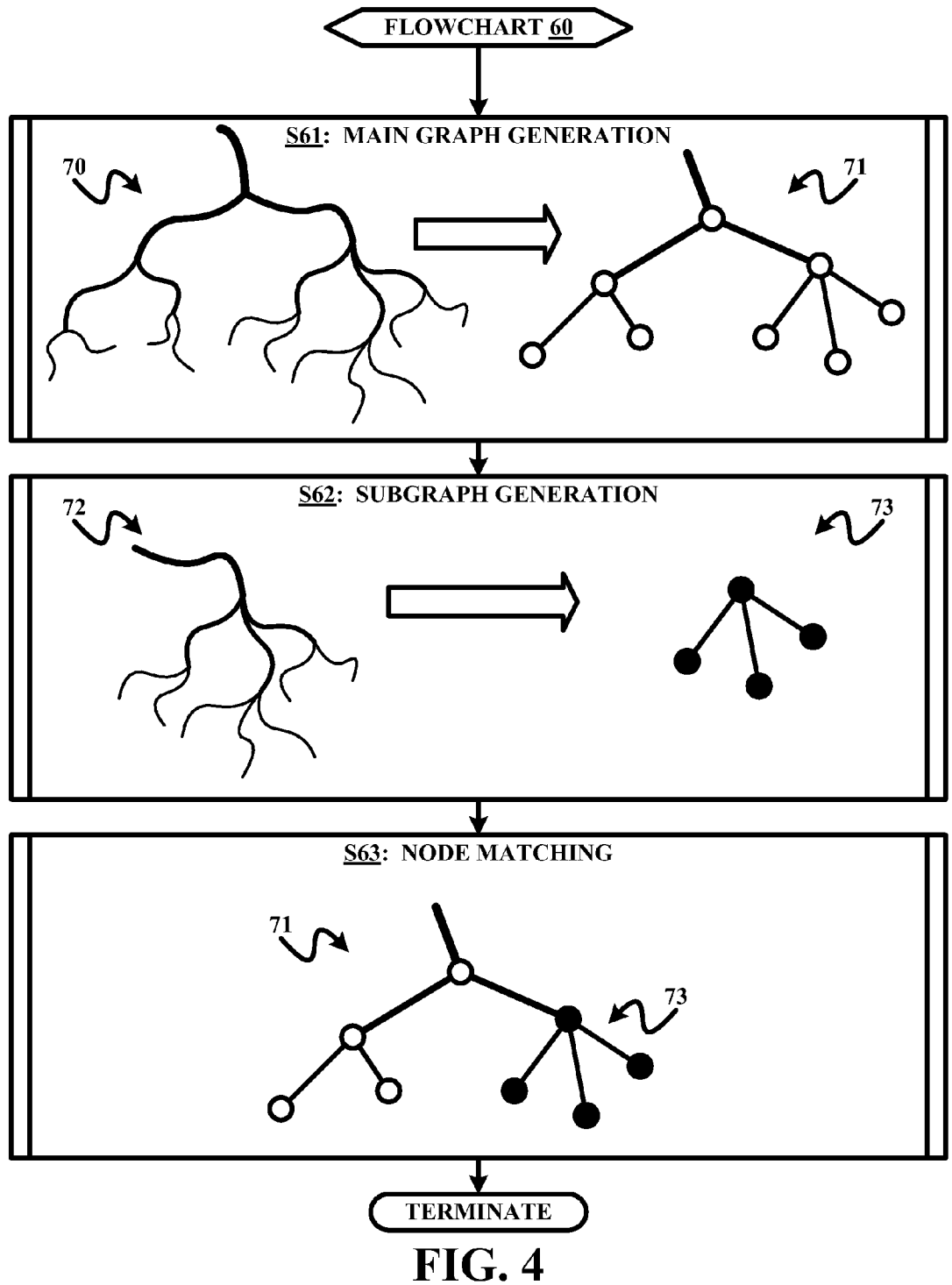
FIG. 4 illustrates a flowchart representative of an exemplary embodiment of a graph matching method in accordance with the present invention.

Referring to FIG. 4, the blood vessel a stage S61 of flowchart 60 encompasses image processing module 23 generating a coronary arterial tree main graph from a geometrical representation of the coronary arterial tree in accordance with any representation method known in the art. For example, as shown in stage S61, a geometrical representation 70 of a coronary arterial tree is converted into a main graph 71 having nodes represented of each furcation (e.g., a bifurcation or trifurcation) of coronary arterial tree geometrical representation 70 and further having branch connections between nodes. Stage S61 may be performed pre-operatively (e.g., days before the endoscopic surgery or any time prior to an introduction of endoscope 12 within patient 50), or intra-operatively by means of a C-arm angiography or other suitable system.

A stage S62 of flowchart 60 encompasses image processing module 23 generating a coronary arterial tree subgraph from a portion of a coronary arterial tree visible in an intra-operative endoscopic image 14 in accordance with any graphical representation method known in the art. Specifically, endoscope 12 is introduced into patient 50 whereby image processing module 23 performs a detection of a coronary arterial structure within the intra-operative endoscopic image 14. In practice, some arterial structures may be visible while other arterial structures may be hidden by a layer of fatty tissue. As such, image processing module 23 may implement an automatic detection of visible coronary arterial structure(s) by known image processing operations (e.g., threshold detection by the distinct red color of the visible coronary arterial structure(s)), or a surgeon may manually use an input device to outline the visible coronary arterial structure(s) on the computer display. Upon a detection of the arterial structure(s), image processing module 23 generates the coronary arterial tree subgraph in a similar manner to the generation of the coronary arterial tree main graph. For example, as shown in stage S62, a geometrical representation 72 of coronary arterial structure(s) is converted into a graph 73 having nodes represented of each furcation (e.g., a bifurcation or trifurcation) of coronary arterial tree geometrical representation 72 and further having branch connections between nodes. Since both trees are coming from the same person, it is understood that the graph derived from endoscopy images is a subgraph of the main graph derived from 3D images.

A stage S63 of flowchart 60 encompasses image processing module 23 matching the subgraph to the maingraph in accordance with any known graph matching methods (e.g., a maximum common subgraph or a McGregor common subgraph). For example, as shown in stage S63, the nodes of subgraph 73 are matched to a subset of nodes of main graph 71.

In practice, subgraph 73 may only be partially detected within intra-operative endoscopic image 14 or some nodes/connections of subgraph 73 may be missing from intra-operative endoscopic image 14. To improve upon the matching accuracy of stage S62, an additional ordering of main graph 71 and subgraph 73 may be implemented.

Figure 5:
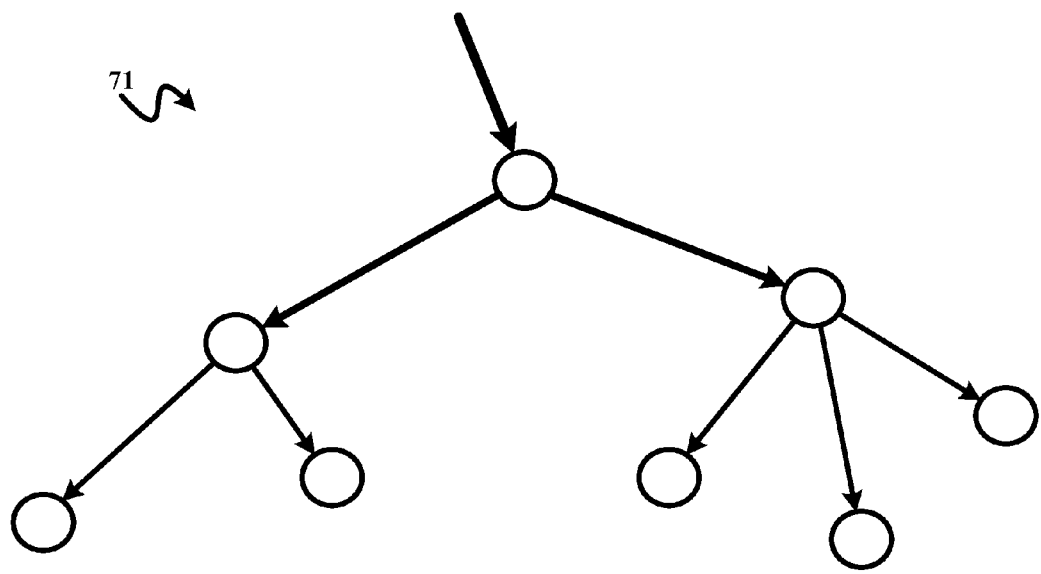
FIGS. 5 and 6 illustrate an exemplary ordering of main graphs of a vessel tree in accordance with the present invention.

In one embodiment, a vertical node ordering of main graph 71 is implemented based on a known orientation of patient 50 during the image scanning of stage S61. Specifically, the main graph nodes may be directionally linked to preserve a top-bottom order as exemplarily shown in FIG. 5 via the solid arrows. For subgraph 73, the orientation of patient 50 relative to endoscope 12 may not be known. However, knowing that branches of the coronary arterial tree reduce in diameter as they expand top-bottom, then varying arterial sizes of the arterial branches in intra-operative endoscopic image 14 may indicate orientation.

Figure 6:
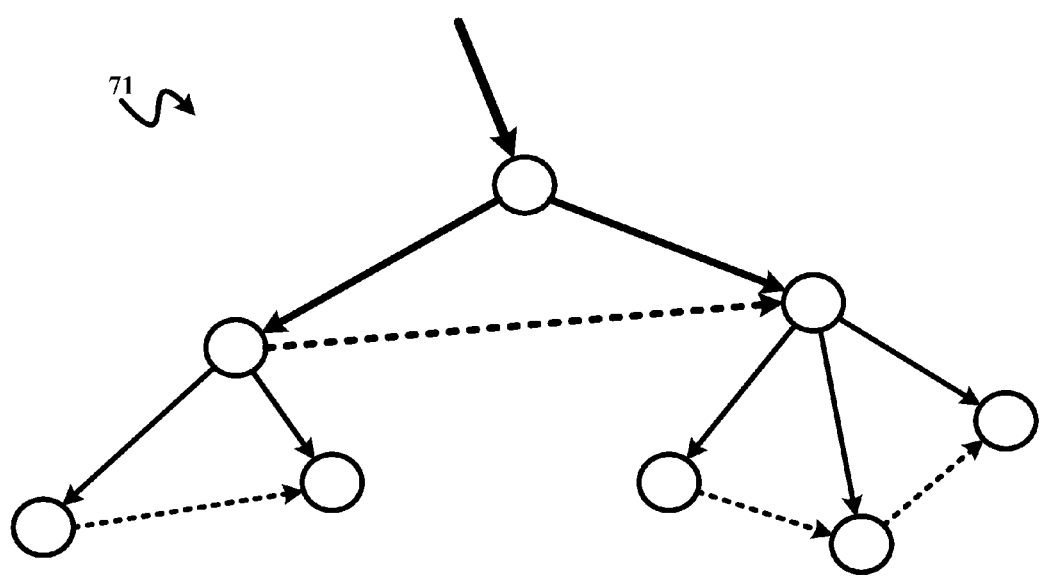

In another embodiment, a horizontal node ordering of main graph 70 may be implemented based on the known orientation of patient 50 during the image scanning of stage S61. Specifically, the main graph nodes may be directionally linked to preserve a left-right node order as exemplarily shown in FIG. 6 via the dashed arrows. For subgraph 73, with the orientation of patient 50 to endoscope 12 more than likely being unknown, the horizontal node order of subgraph 73 may be set by the operating surgeon or an assistant via a graphical user interface.

While the use of ordering may decrease the time for matching the graphs and reduce the number of possible matches, theoretically multiple matches between the graphs may still be obtained by the matching algorithm. Such a case of multiple matches is addressed during a stage S33 of flowchart 30.

Referring again to FIG. 2, based on the matching of the graphs, a stage S33 of flowchart encompasses an overlay of the geometrical representation of pre-operative 3D image 44 (FIG. 1) of the vessel tree on the intra-operative endoscopic image 14 of the vessel tree. This is done by using the geometrical representation uniquely associated to the maingraph.

Thus, the entire geometry may be directly translated to intra-operative endoscopic image 14 using a perspective transformation. The perspective transformation may be detected from intra-operative endoscopic image 14 and nodes in pre-operative 3D image 44 using matching algorithms known in art (e.g., a homography matching).

Figure 7:
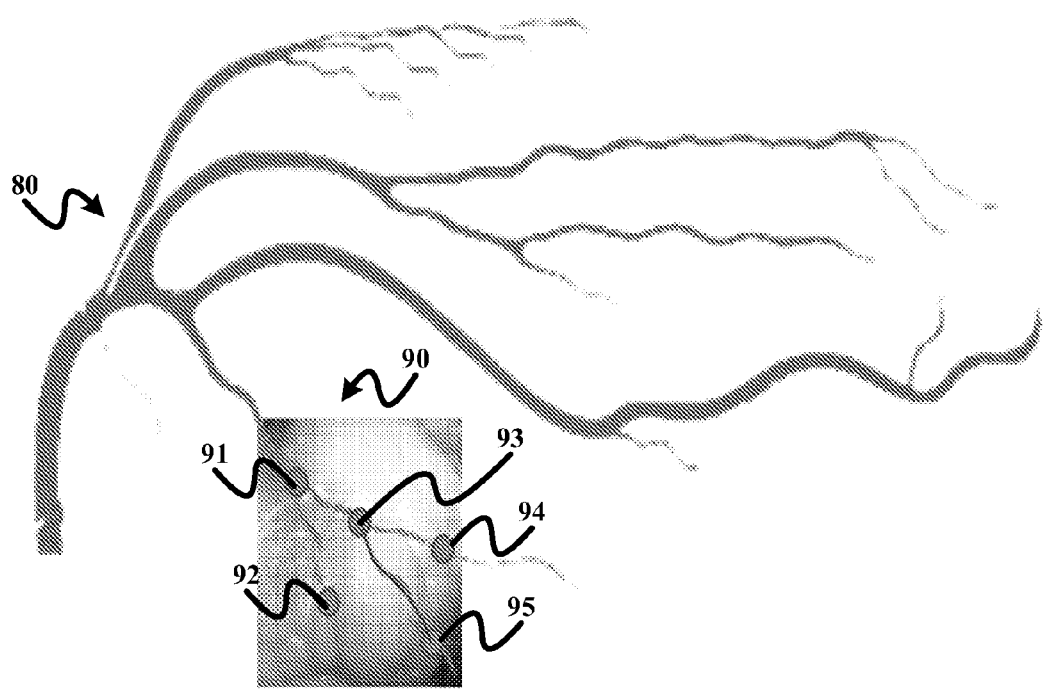
FIG. 7 illustrates an exemplary overlay of geometrical representation on endoscopic image accordance with the present invention.
Figure 8:
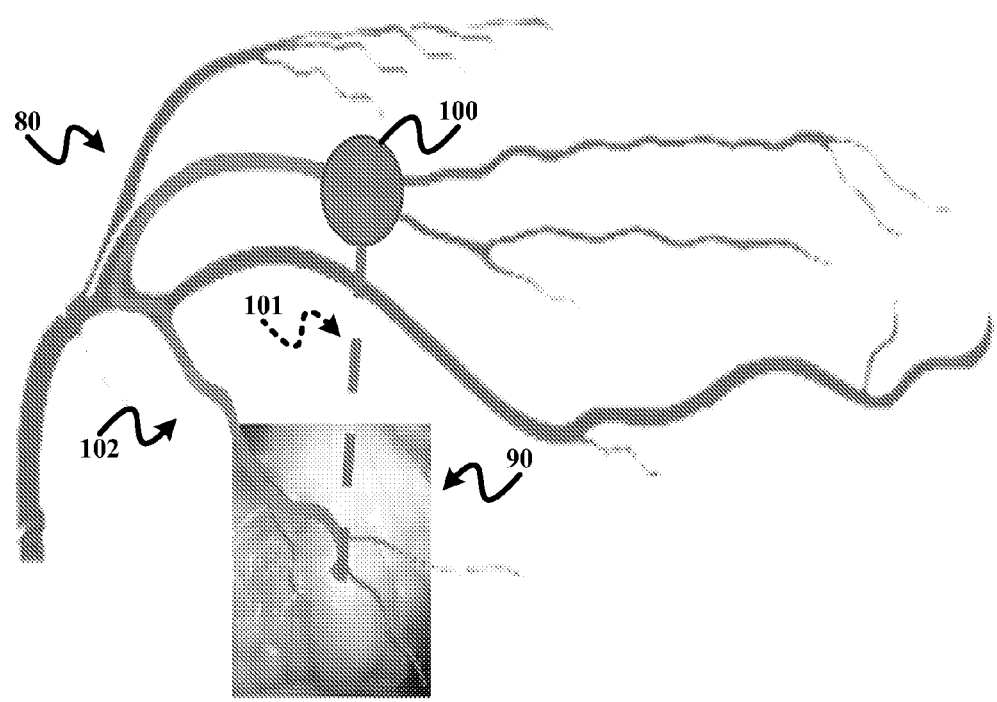
FIG. 8 illustrates an exemplary robot path within the overlay shown in FIG. 7 in accordance with the present invention.

For example, FIG. 7 illustrates a geometrical representation 80 of a coronary arterial tree having nodes matched to nodes 91-95 with an intra-operative endoscopic image 90. The distance between each node pair among nodes 91-95 may be used to determine a scaling factor for geometrical representation 80 to thereby enable geometrical representation 80 to overlay intra-operative endoscopic image 90 as shown.

In practice, if the graph matching of stage S32 (FIG. 2) yields multiple results, then all possible overlays may be displayed to the surgeon whereby the surgeon may select the matching result the surgeon believes is the most likely match via a graphical user interface. Given that the surgeon knows the position of endoscope 12 relative to at least some structures in intra-operative endoscopic image 14, the selection may be relatively straightforward.

Referring back to FIG. 2, a stage S34 of flowchart 30 encompasses visual servo module 24 generating an endoscopic path within the overlay of the geometrical representation of pre-operative 3D image 44 (FIG. 1) of the vessel tree on intra-operative endoscopic image 14 (FIG. 1) of the vessel tree. Based on the endoscopic path, visual servo module 24 generates endoscope position commands 25 to robot controller 21 to thereby guide endoscope 12 (FIG. 1) along the endoscopic path to a desired position within the anatomical region. Specifically, once the exact overlay is found, robot 11 may be commanded to guide endoscope 12 to positions the surgeon selects on pre-operative 3D image 44. The surgeon or the assistant may select a point of vessel tree, and robot 11 may guide endoscope 12 towards that desired position along any suitable path.

Figure 9:
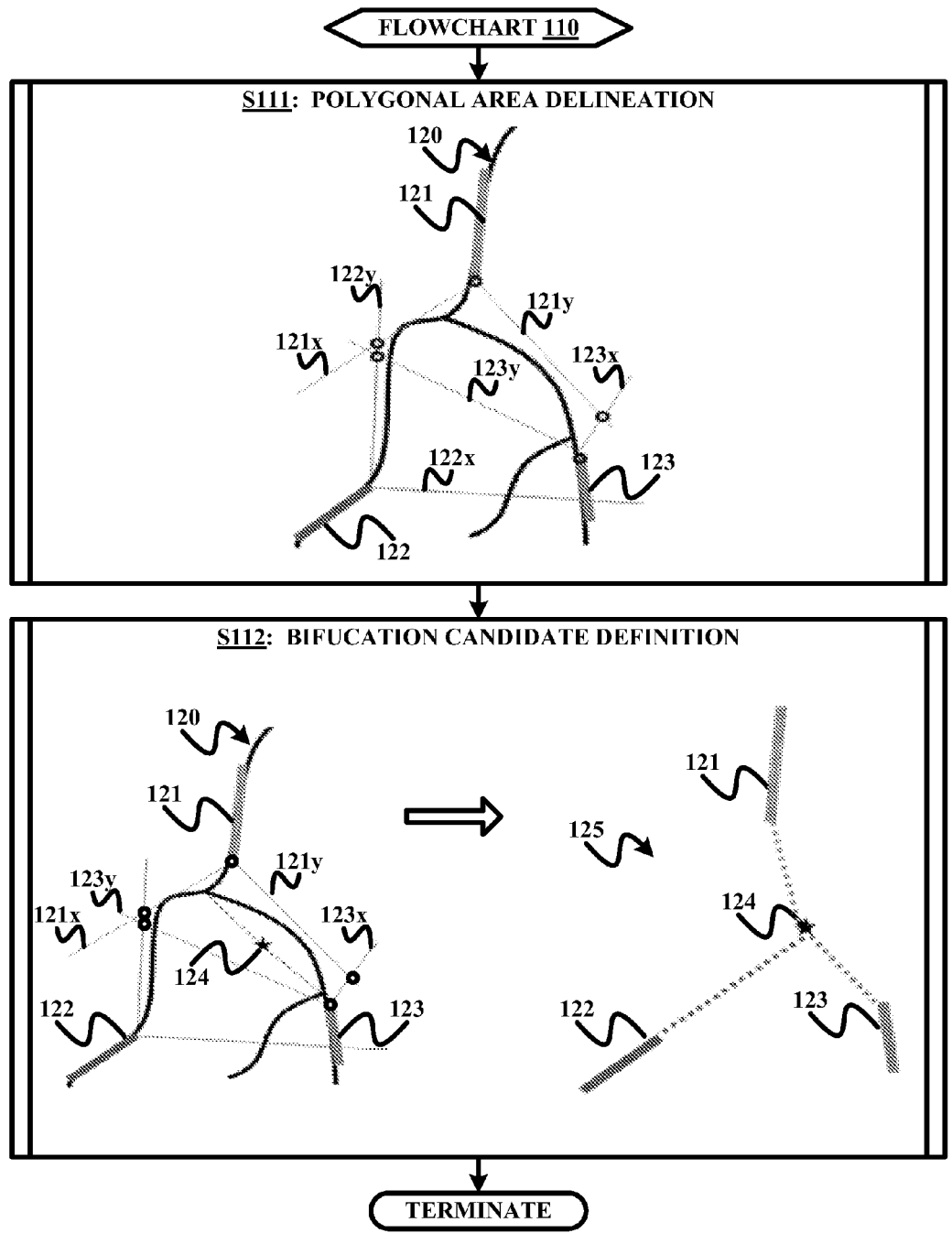
FIG. 9 illustrates a flowchart representative of an invisible bifurcation detection method in accordance with the present invention.

For example, as shown in FIG. 9, robot 11 may move endoscope 12 along a shortest path 101 to a desired position 100 or along a coronary arterial path 102 to desired position 100. Coronary arterial path 102 is the preferred embodiment, because coronary arterial path 102 allows the surgeon to observe visible arteries as robot 11 moves endoscope 12. In addition, it might help the surgeon to decide if the matching was successful. Coronary arterial path 102 may be defined using methods known in art (e.g., Dijkstra shortest path algorithm).

In practice, the movement of robot 11 may be commanded using uncalibrated visual servoing with remote center of motion, and the field of view of endoscope 12 may be extended to enable a larger subgraph during matching stage S32 (e.g., a stitching of intra-operative endoscopic images 14 as known in the art).

As previously described herein, stages 32 and 33 of flowchart 30 as shown in FIG. 2 represents a vessel tree image registration of the present invention involving a single vessel tree. Additionally, the previous description of stages S32 and S33 was provided in the context of a coronal arterial tree to facilitate an understanding of stages S32 and S33. In practice, vessel tree image registration of the present invention may involve two (2) or more blood vessels trees of any type within any anatomical region of the body.

Referring back to FIG. 2, stage S32 uses furcation points visible in the endoscope view for matching of vessel tree (e.g., arterial tree) from preoperative data 44 (FIG. 1) to endoscopy video (FIG. 1). In practice, as previously stated herein, a total number of visible furcations may not be sufficient to perform an accurate matching of the vessel tree from preoperative data 44 to endoscopy video 14. Also, geometrical information of the vessel tree (e.g., shape of visible branches in endoscopy image 14) may be incapable of being translated to geometric terms given that endoscope 12 is typically not calibrated, and any calibration of endoscope 12 may cause significant disruptions in the workflow.

FIGS. 9-12 illustrate additional embodiments of stage S32 for detecting furcations that may not be visible in the endoscope video 14 from visible branches of the vessel tree, particularly for the detection of arterial bifurcations invisible in the endoscope video 14 from visible segments of arteries. These embodiments perform graph generation and node matching in accordance with the principles of flowchart 60 (FIG. 4) as previously taught herein.

Referring to FIG. 9, a flowchart 110 represents a method for detecting furcations that may not be visible in the endoscope video from visible branches of the vessel tree that serves as a basis for registering intra-operative endoscopic images of the anatomical region to a pre-operative 3D image of the anatomical region. To facilitate an understanding this method, flowchart 110 will be described herein in the context of a bifurcation that is not visible in an endoscopic view due to being covered with fatty tissue or by heart muscle (intra-myocardial arteries), which is very common in patients requiring coronary bypass surgery.

A stage S111 of flowchart 110 encompasses a utilization of branch segments of an arterial tree visible in an endoscopic view to construct a polygon possibly enclosing a bifurcation invisible in the endoscopic view.

Specifically, stage S111 involves a surgeon or any support staff to manually mark the visible segments of the arterial tree shown in the endoscopic video. For example, stage S111 shows a sub-tree 120 of an arterial tree with three (3) marked arterial segments 121-123 visible in an endoscopic video with the rest of the arterial tree being covered with fat, particularly both bifurcations of sub-tree 120.

Stage S111 further involves a definition of rays extending from marked visible branch segments for purposes of delineating a polygonal area enclosing the invisible bifurcation(s) of the arterial tree. For example, stage S111 shows rays 121$x$-121$y$ extending from segment 121, rays 122$x$-122$y$ extending from segment 122 and rays 123$x$-123$y$ extending from segment 123 for delineating an area enclosing the invisible bifurcations of sub-tree 120. In practice, an angle between each ray and corresponding segment may be predefined knowing that arteries run from top of the heart down because it is not expected that an artery will abruptly change direction and start going up). Also, maximal possible angles may be extracted from preoperative 3D scan of the arterial tree.

For any triplet of segments as exemplary shown in stage S111, there is at most one polygonal area (marked with circles) where all rays from all the segments are overlapping. This is the enclosed area where it is expected to find the bifurcations of sub-tree 120. If there was no overlap between the rays, then it is likely that marked branch segments 121-123 belong to the same arterial branch and that there is no bifurcations or that marked branch segments 121-123 belong to very different branches.

From the delineated polygonal area of stage S111, a stage S112 of flowchart 110 encompasses a definition of a bifurcation within the polygonal area. In one embodiment, as shown in stage S112, a center 124 of the polygonal area may be defined as a bifurcation. In an alternate embodiment, the delineated polygonal area may be made visible on the endoscope images. The surgeon with his/her knowledge of anatomy or nearby anatomical structures and/or from the pre-operative scan data, may then manually select a point within the polygonal area which he/she thinks will be the most probably location for the bifurcation point. More particularly, if one of the selected vessels can be anatomically identified (e.g., a left anterior descending artery), then observing the pre-operative image around that vessel structure may lead to a good guess of the possible bifurcation within the polygonal area.

Once the bifurcation point has been calculated or selected, then a graphical representation of the vessel structure using the new bifurcation point may be generated. For example, stage S112 shows a graphical representation 125 based on bifurcation 124 as defined by the visible branch segments 121-123. This graphical representation 125 may serve as a subgraph or part of a larger sub-graph for purposes of flowchart 60 (FIG. 4).

In practice, given that the coronary arteries are well defined anatomical structures with standard shape and morphology over most patients, an unreasonable graphical representation would indicate a fault in the defined bifurcation point. For example, if bifurcation point 124 required a certain vessel segment 122 to make an extreme curve that is highly unlikely in view of the anatomical structure of arterial trees, then graphical representation 125 would deemed to be unreasonable if view of a faulty bifurcation point 124. In the case, graphical representation 125 may be discarded and flowchart 110 may be re-executed.

Figure 10:
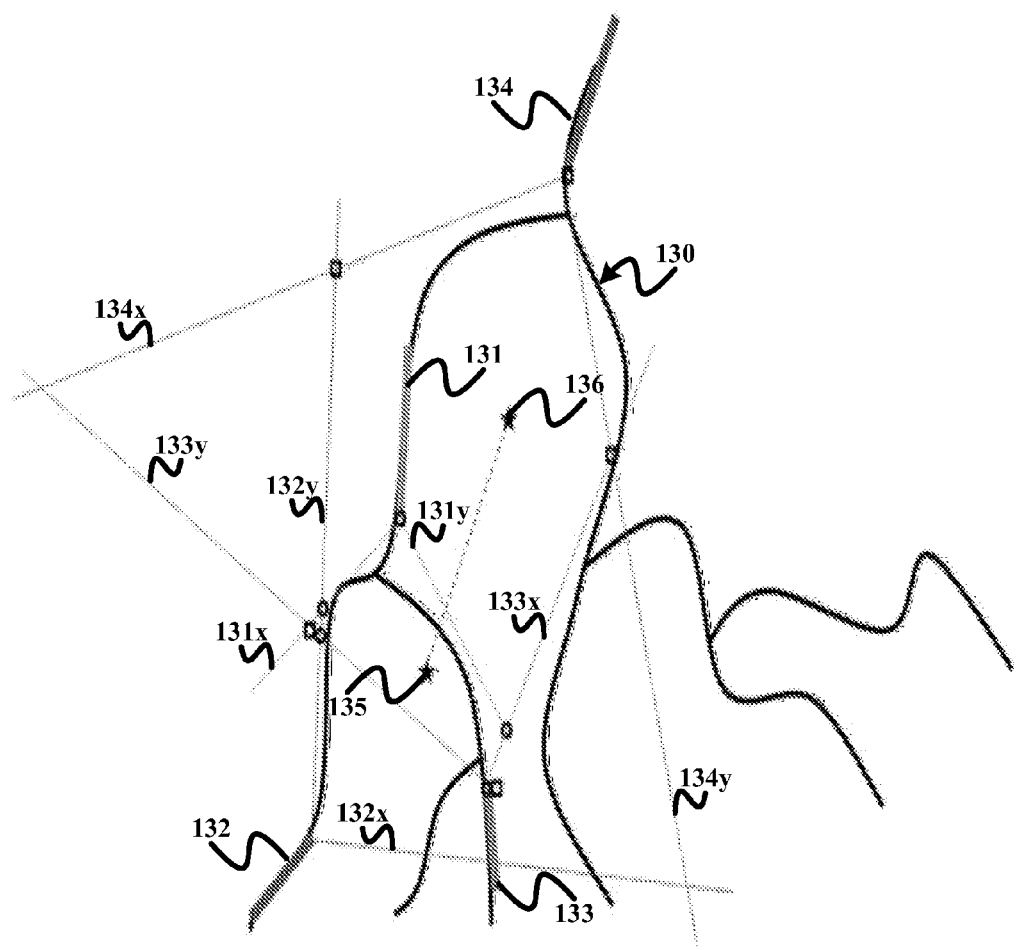
FIG. 10 illustrates an exemplary bifurcation detection of a multi-bifurcation vessel tree in accordance with the flowchart illustrated in FIG. 9.

To facilitate a further understanding of flowchart 110, FIG. 10 illustrates a marking of four (4) visible branch segments 131-134 of a sub-tree 130 of an arterial tree. A total of four (4) candidate polygonal areas are delineated from all possible combination from overlapping x-y rays of segments 131-134. Specifically, x-y rays of segments 131-132-133 form a first polygonal area, x-y rays from segments 132-133-134 form a second polygonal area, x-y rays of segments 132-134 from a third polygonal area, and x-y rays of segments 133-134 form a fourth polygonal area. Of these four (4) polygonal areas, only the first polygonal area and the second polygonal area are valid because these polygonal areas involve the overlapping of three (3) segments. A bifurcation candidate 135 is a center of polygonal area 131-132-133 and bifurcation candidate 136 is a center of polygonal area 132-133-134. As polygonal area 131-132-133 is within polygonal area 132-133-134, the two (2) bifurcation candidates 135 and 136 may be assumed to be connected through a $1^{st}$ order tree (dotted line).

Figure 11:
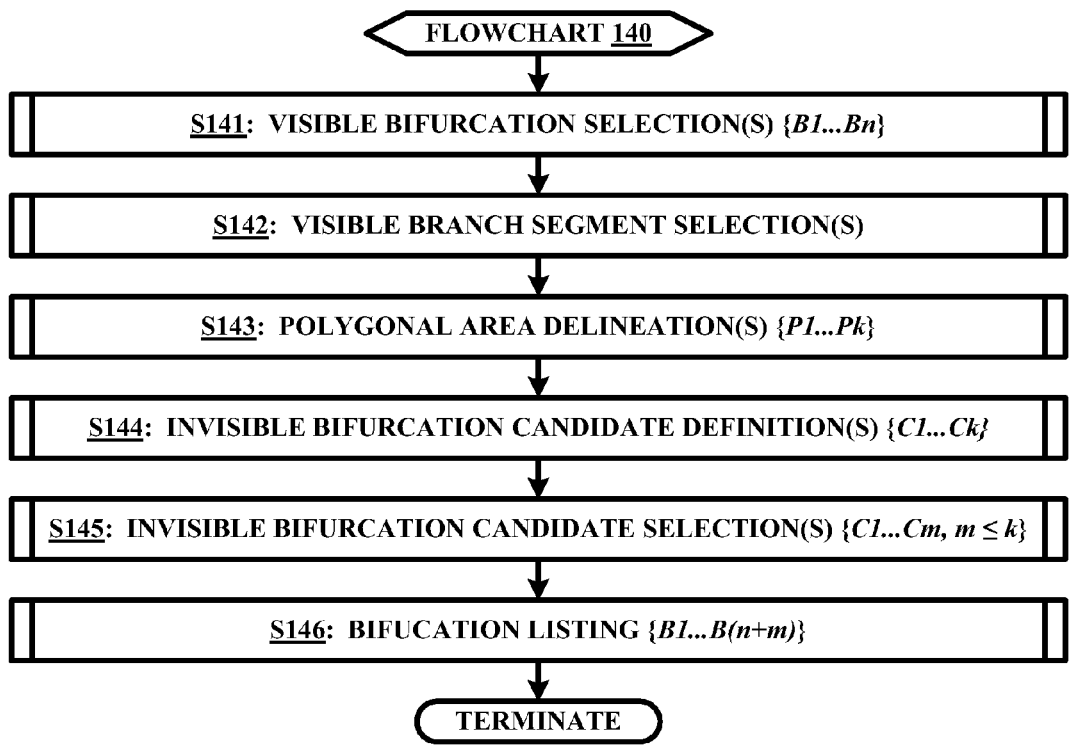
FIG. 11 illustrates a flowchart representative of a visible/invisible bifurcation registration method in accordance with the present invention.

In practice, an endoscopic image of an arterial tree may have visible bifurcations and invisible bifurcations. FIG. 11 illustrates a flowchart 140 representative of a visible/invisible bifurcation registration method for generating a subgraph in accordance with flowchart 60 (FIG. 4).

A stage S141 of flowchart 140 encompasses a selection on n bifurcation(s) B visible in the endoscopic image. A stage S142 of flowchart 140 encompasses a selection of all visible branch segments in the endoscopic image in accordance with flowchart 110 (FIG. 9). From the selected visible branch segments, a stage S143 of flowchart 140 encompasses a delineation of k polygonal area(s) P and a stage S144 of flowchart 140 encompasses a definition of k invisible bifurcation candidates C.

A stage S145 of flowchart 140 encompasses a comparison all n visible bifurcations B to all k candidates of invisible bifurcations C. If any of pairing (B, C) of bifurcations belong to the same polygonal area, then it is likely that the invisible bifurcation is predicting the visible bifurcation, and it is discarded. All remaining m invisible bifurcations are combined to build a final bifurcation list during stage S146 of flowchart 140 whereby a subgraph may be generated from the final bifurcation list for flowchart 60.

Figure 12:
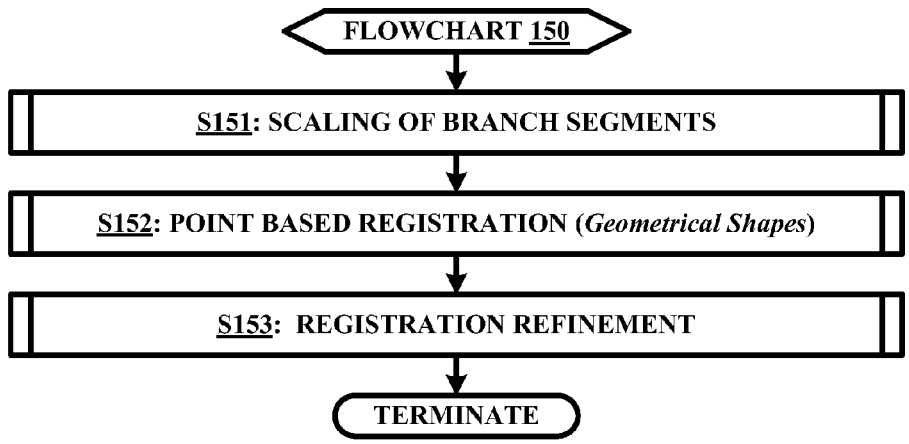
FIG. 12 illustrates a flowchart representative of a bifurcation registration refinement method in accordance with the present invention.

Referring to FIG. 9, a shape of an arterial tree is impractical to use directly when marking the visible branch segments, because clinical endoscopes are usually not calibrated and additional calibration may cause significant disruptions in the workflow. Thus, the scale of the shape of the arterial tree is unknown. FIG. 12 illustrates a flowchart 150 representative of a registration refinement method that retrieves a scale of objects in endoscope images from the pre-operative 3D image after the initial image registration is performed via stage S32 (FIG. 2) and arteries from the preoperative 3D images are overlaid on the endoscope images via stage S33 (FIG. 2). For example, it is possible to retrieve length in SI units of any artery segment objects in endoscope images from the pre-operative 3D image.

Specifically, a stage S152 of flowchart 150 encompasses a retrieval of a scale of objects, particularly arteries, after the overlay is performed, scale of objects and a scaling of the shape of artery segments in world units (e.g. millimeters) instead of pixels. These shapes are utilized during a stage S153 of flowchart 150 to perform a point-based registration (e.g., an Iterative Closest Point (ICP) known in art), which in turns is used to refine the initial image registration of stage S32.

Referring back to FIG. 1, in practice, modules 23 and 24 may be implemented by hardware, software and/or firmware integrated within endoscope controller 22 as shown.

From the description of FIGS. 1-12 herein, those having ordinary skill in the art will appreciate the numerous benefits of the present invention including, but not limited to, an application of the present invention to any type of endoscopy surgery performed on any type of blood vessels.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:
1. An image registration system, comprising:
an endoscope (12) operable for generating an intra-operative endoscopic image (14) of a vessel tree within an anatomical region,
wherein the intra-operative endoscopic image (14) of the vessel tree includes a plurality of branches of the vessel tree visible within the intra-operative endoscopic image (14) as an indication of a furcation of the vessel tree invisible within the intra-operative endoscopic image (14); and
an endoscope controller (22) operable for image registering the intra-operative operative endoscopic image (14) of the vessel tree to a pre-operative three-dimensional image (44) of the vessel tree within the anatomical region,
wherein the image registration includes an image matching of a graphical representation of the furcation of the vessel tree as indicated by the visible branches of the vessel tree within the intra-operative endoscopic image (14) of the vessel tree to a graphical represen- tation of the furcation of the vessel tree within the pre-operative three-dimensional image (44) of the vessel tree.

2. The image registration system of claim 1, wherein the image matching includes:
   generating a main graph derived from a geometrical representation of the pre-operative three-dimensional image (44) of the vessel tree, the main graph including a main set of nodes representative of each furcation of the vessel tree within the pre-operative three-dimensional image (44) of the vessel tree;
   generating a subgraph derived from a geometrical representation of the intra-operative endoscopic image (14) of the vessel tree, the subgraph including a subset of the main set of nodes, wherein a first node of the subset is representative of the furcation of the vessel tree as indicated by the visible branches of the vessel tree within the intra-operative endoscopic image (14) of the vessel tree; and
   node matching the subgraph to the main graph.

3. The image registration system of claim 2, wherein the image matching of the subgraph to the main graph includes:
   establishing at least one of a vertical ordering and a horizontal ordering of the nodes in the main graph.

4. The image registration system of claim 1, wherein the image registration further includes:
   delineating a polygonal area on the intra-operative endoscopic image (14) enclosing the furcation of the vessel tree invisible within the intra-operative endoscopic image (14).

5. The image registration system of claim 4, wherein a delineation of the polygonal area includes:
   marking each branch of the vessel tree visible within the intra-operative endoscopic image (14) as a branch segment;
   extending rays from each branch segment; and
   delineating overlapping rays of different branch segments.

6. The image registration system of claim 4, wherein the image registration further includes:
   defining a furcation candidate within the polygonal area as a detection of the furcation of the vessel tree invisible within the intra-operative endoscopic image (14).

7. The image registration system of claim 6, wherein a definition of the furcation candidate within the polygonal area includes:
   identifying a center of the polygonal area as the furcation candidate.

8. The image registration system of claim 6, wherein a definition of the furcation candidate within the polygonal area includes:
   identifying a point within the polygonal area as the furcation candidate based on an anatomy of the anatomical region.

9. The image registration system of claim 6, wherein a definition of the furcation candidate within the polygonal area includes:
   identifying a point within the polygonal area as the furcation candidate based pre-operative three-dimensional image (44) of the vessel tree.

10. The image registration system of claim 1,
    wherein the image registration further includes:
       selecting all visible furcations within the intra-operative endoscopic image (14); and
    wherein the image matching includes:
       generating a geometrical representation of the intra-operative endoscopic image (14) of the vessel tree utilizing the visible furcations and the invisible furcation.

11. The image registration system of claim 10, wherein the image registration further includes:
    delineating a polygonal area on the intra-operative endoscopic image (14) enclosing the invisible furcation of the vessel tree, wherein the visible furcations are external to the polygonal area.

12. The image registration system of claim 1, the endoscope controller (22) is further operable for refining an image registration of the intra-operative operative endoscopic image (14) of the vessel tree to a pre-operative three-dimensional image (44) of the vessel tree based on a scale of the vessel tree within the pre-operative three-dimensional image (44) of the vessel.

13. The image registration system of claim 1, wherein a refinement of the image registration includes:
    utilizing the scale of the vessel tree within the pre-operative three-dimensional image (44) of the vessel to scale of a shape of each branch of the vessel tree visible within the intra-operative operative endoscopic image (14); and
    utilizing a scale a shape of each branch of the vessel tree visible within the intra-operative operative endoscopic image (14) to execute a point-based registration of the intra-operative endoscopic image (14) of the vessel tree to the pre-operative three-dimensional image (44) of the vessel tree.

14. The image registration system of claim 1, wherein the endoscope controller (22) is further operable for overlaying the geometrical representation of the pre-operative three-dimensional image (44) of the vessel tree onto the intra-operative endoscopic image (14) of the vessel tree in accordance with the image registration.

15. The image registration system of claim 1, wherein the vessel tree is one of an arterial tree and a venous tree.

* * * * *